United States Patent [19]

Warriner

[11] Plant 4,648

[45] Feb. 17, 1981

[54] ROSE PLANT

[75] Inventor: William A. Warriner, Tustin, Calif.

[73] Assignee: Jackson & Perkins Co., Medford, Oreg.

[21] Appl. No.: 90,670

[22] Filed: Nov. 2, 1979

[51] Int. Cl.[3] ..... A01H 5/00

[52] U.S. Cl. ..... Plt./11

[58] Field of Search ..... Plt./11

*Primary Examiner*—Robert E. Bagwill

*Assistant Examiner*—James R. Feyrer

*Attorney, Agent, or Firm*—Klarquist, Sparkman, Campbell, Leigh, Hall & Whinston

[57] ABSTRACT

Rose plant of hybrid tea class resulting from cross of Futura, U.S. Plant Pat. No. 3,569 with First Prize, U.S. Plant Pat. No. 2,774. Plant is vigorous, taller than First Prize and similar to Futura. Bud is red, changing to pink in blossom.

1 Drawing Figure

This present invention relates to a new and distinct variety of rose plant of the hybrid tea class which was originated by me by crossing the variety Futura, U.S. Plant Pat. No. 3,569 with pollen of the variety First Prize, U.S. Plant Pat. No. 2,774.

The primary objective of this breeding was to produce a new rose variety, of the hybrid tea class, combining the growth characteristics of Futura with bloom characteristics of First Prize. This objective was substantially achieved along with other desirable improvements as evidenced by the following unique combination of characteristics which are outstanding in the new variety and which distinguish it from its parents as well as from all other varieties of which I am aware:

1. A vigorous, upright habit of growth, taller than that of First Prize and similar to that of Futura.
2. An abundance of leathery foliage having broad, oval leaflets similar to those of Futura.
3. Bud color of a red similar to RHSCC 47A.
4. Flower color generally similar to RHSCC 54B aging to a lighter pink similar to RHSCC 49D.

Asexual reproduction of this new variety by budding as performed at Wasco, Calif., shows that the foregoing characteristics and distinctions are established and are transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with Royal Horticultural Society Colour Chart except where ordinary dictionary significance of color is indicated.

Parentage:
- *Seed parent.*—Futura.
- *Pollent parent.*—First Prize.

Classification:
- *Botanical.*—Rosa hybrid.
- *Commercial.*—Hybrid Tea.

FLOWER

Observations made from specimens grown outside at Irvine, Calif., in August.

Blooming habit: Continuous.

Bud:
- *Size.*—1" to 1¼" when petals start to unfurl.
- *Form.*—Pointed ovoid.
- *Color.*—When sepals first divide, RHSCC 47A; when half blown, upper side of petals RHSCC 54B; lower side of petals RHSCC 47A.
- *Sepals.*—Color: Outer surface RHSCC 138B, stippled and occasionally with RHSCC 187C; three appendaged sepals normally appendaged; two unappendaged sepals hairy edged.
- *Receptacle.*—Color: RHSCC 138B. Shape: Funnel. Size: Broad, small. Surface: Smooth.
- *Peduncle.*—Length: Medium. Surface: Prickly. Color: Light green. Strength: Stiff, erect.
- *Opening.*—Petals fold outward without curling.

Bloom:
- *Size.*—Large. Average open size 5".
- *Borne.*—Singly, occasionally several together.
- *Stems.*—Long, strong.
- *Form.*—When first open, cupped. Permanence: Flattens, outer petal edges slightly curled.
- *Petalage.*—Number of petals under normal conditions: 25 to 30.
- *Color.*—Center of flower: Upper side of petals, when fully open, near RHSCC 49C. Reverse side of petals near RHSCC 51C. Base of petals yellow at point of attachment. General tonality from a distance: Shows the pink RHSCC 49C from above, but the reverse color RHSCC 51C is evident.
- *Variegations.*—None.
- *Discoloration.*—General tonality at end of first day, fades slightly; third day, RHSCC 49D.
- *Fragrance.*—Slight.

Petals:
- *Texture.*—Thick.
- *Shape.*—Round.
- *Form.*—Tips slightly recurved.
- *Arrangement.*—Imbricated. Petaloids in center, few.
- *Persistence.*—Drop off cleanly.
- *Lastingness.*—On the plant, long. As cut flower, long.

Reproductive parts:
- *Anthers.*—Medium. Color, yellow. Arrangement, regular around styles.
- *Filaments.*—Color: Yellow.
- *Pollen.*—Gold yellow.

*Styles.*—Color: Near White.

*Stigmas.*—Color: White.

PLANT

Form: Bush.

Growth: Very vigorous, upright, branching; taller than First Prize, reaching approximately 6′ at Irvine, Calif.

Foliage: Number of leaflets on normal mid-stem leaves: 5.

*Size.*—Medium.

*Quantity.*—Abundant.

*Color.*—New foliage: Near RHSCC 187C. Old foliage: Near RHSCC 133A.

Leaflets:

*Shape.*—Wide oval.

*Texture.*—Leathery.

*Edge.*—Serrated.

*Serrations.*—Single, small.

*Petiole.*—Rachis: Color, reddish. Underside: Prickles.

*Stipules.*—Long, bearded.

*Disease resistance.*—Average resistance to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, many. On laterals from stalk, many.

*Form.* —Narrow base, long, hooked downward.

*Color when young.*—Brown.

*Color when old.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its vigorous, upright, well branched habit of growth, its abundance of leathery foliage and its bud color of RHSCC 47A, the blossom aging from a pink similar to RHSCC 54B to a light pink similar to RHSCC 49D.

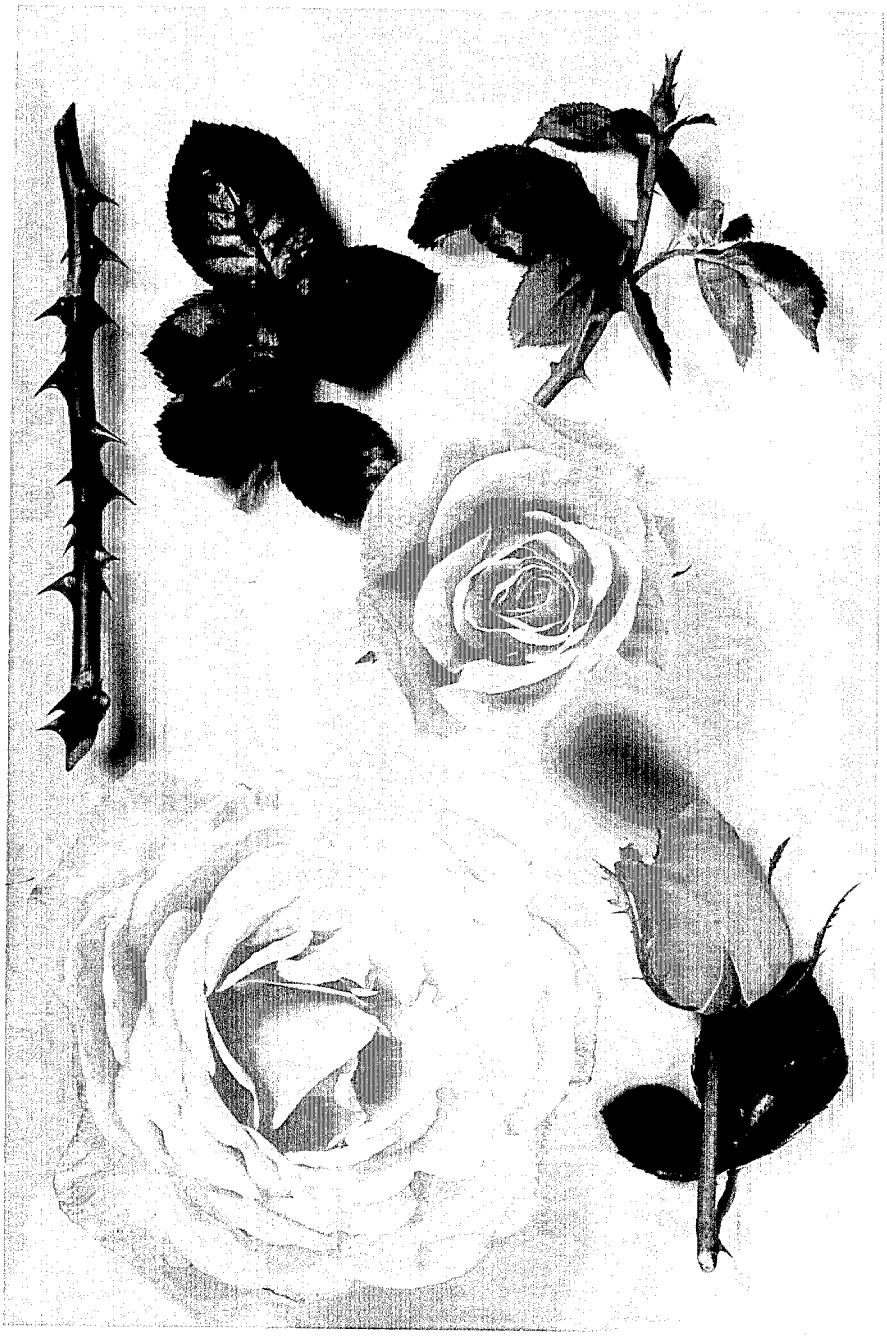

* * * * *